US011187626B2

(12) United States Patent
Nunes Nogueira et al.

(10) Patent No.: US 11,187,626 B2
(45) Date of Patent: Nov. 30, 2021

(54) FERMENTATION MONITORING SYSTEM

(71) Applicant: Watgrid, S.A., Ilhavo (PT)

(72) Inventors: Rogério Nunes Nogueira, Gafanha da Boa Hora (PT); Lúcia Maria Botas Bilro, Gafanha da Encarnação (PT); Fábio Patricio Domingues Gonçalves, Pombal (PT); Pedro Miguel Estima da Costa, Aveiro (PT); Ricardo José Ventura de Sousa e Carvalho Pereira, Oporto (PT)

(73) Assignee: Watgrid, S.A.

( * ) Notice: Subject to any disclaimer, the term of this patent is extended or adjusted under 35 U.S.C. 154(b) by 86 days.

(21) Appl. No.: 16/686,595

(22) Filed: Nov. 18, 2019

(65) Prior Publication Data

US 2020/0158602 A1 May 21, 2020

Related U.S. Application Data (60) Provisional application No. 62/769,648, filed on Nov. 20, 2018.

(51) Int. Cl.
  *G01N 1/12* (2006.01)
  *G01N 33/14* (2006.01)
  *G01N 1/10* (2006.01)

(52) U.S. Cl.
  CPC ............. *G01N 1/12* (2013.01); *G01N 33/146* (2013.01); *G01N 2001/1037* (2013.01)

(58) Field of Classification Search
  CPC ............. G01N 1/12; G01N 2001/1037; G01N 33/146; C12H 1/22; C12G 1/00
  See application file for complete search history.

(56) References Cited

U.S. PATENT DOCUMENTS

| | | | |
|---|---|---|---|
| 4,368,639 A | 1/1983 | Owens | |
| 4,984,451 A | 1/1991 | Wilen | |
| 5,108,123 A * | 4/1992 | Rubenzik | B60D 1/36 280/477 |
| 5,894,856 A * | 4/1999 | Swenson | F16K 17/363 137/38 |
| 5,953,954 A | 9/1999 | Drain | |
| 6,647,922 B1 * | 11/2003 | Travis | A01K 45/002 119/69.5 |
| 2003/0219062 A1 | 11/2003 | Egidio | |
| 2004/0076946 A1 * | 4/2004 | Trauner | G01N 33/146 435/3 |
| 2004/0079152 A1 * | 4/2004 | Sorenson | G01F 23/38 73/313 |

(Continued)

FOREIGN PATENT DOCUMENTS

| | | |
|---|---|---|
| CN | 204214506 | 3/2015 |
| EP | 1270716 | 1/2003 |

(Continued)

OTHER PUBLICATIONS

Int'l Search Report and Written Opinion Appln No. PCT/IB2019/001252 dated Apr. 23, 2020.

(Continued)

*Primary Examiner* — Natalie Huls (74) *Attorney, Agent, or Firm* — McAndrews, Held & Malloy, Ltd.

(57) ABSTRACT

Aspects of a monitoring system for winemaking are provided.

18 Claims, 7 Drawing Sheets

(56) References Cited

U.S. PATENT DOCUMENTS

| | | | | |
|---|---|---|---|---|
| 2011/0101010 | A1* | 5/2011 | Maiocco | C12H 1/22 |
| | | | | 220/720 |
| 2014/0081580 | A1* | 3/2014 | Kim | G01N 33/0004 |
| | | | | 702/24 |
| 2015/0198474 | A1* | 7/2015 | Howard | C12G 1/00 |
| | | | | 702/55 |
| 2015/0253174 | A1* | 9/2015 | Barrett | C12H 1/22 |
| | | | | 73/304 C |
| 2015/0377681 | A1* | 12/2015 | Kleman | G01F 25/0061 |
| | | | | 73/290 V |
| 2017/0028800 | A1* | 2/2017 | Ghannam | B60D 1/64 |
| 2020/0157479 | A1* | 5/2020 | Nunes Nogueira | C12M 41/12 |
| 2020/0158708 | A1* | 5/2020 | Nunes Nogueira | |
| | | | | G01F 23/0061 |

FOREIGN PATENT DOCUMENTS

| | | | |
|---|---|---|---|
| WO | 2013028144 | A3 | 2/2013 |
| WO | 2017091088 | A1 | 6/2017 |
| WO | 2017216746 | | 12/2017 |

OTHER PUBLICATIONS

Int'l Search Report and Written Opinion Appln No. PCT/IB2017/053549 dated Oct. 5, 2017 (6 pgs).

N. Oliveiram et al., Winegrid®: the remote and real-time wine production process monitoring system (6 pgs).

Portuguese Search Report Appln No. 109451 dated Nov. 18, 2016 (2 pgs).

Int'l Preliminary Report on Patentability Appln No. PCT/IB2019/001252 dated Jun. 3, 2021.

* cited by examiner

Bung 603
Top View

Fig. 7B

Bung 603
Side View

Fig. 7C

Bung 603
Bottom View

FERMENTATION MONITORING SYSTEM

BACKGROUND

Limitations and disadvantages of conventional and traditional monitoring systems for winemaking will become apparent to one of skill in the art, through comparison of such systems with some aspects of the present invention as set forth in the remainder of the present application with reference to the drawings.

BRIEF SUMMARY OF THE INVENTION

Monitoring systems for winemaking substantially as shown in and/or described in connection with at least one of the figures, as set forth more completely in the claims.

These and other advantages, aspects and novel features of the present invention, as well as details of an illustrated embodiment thereof, will be more fully understood from the following description and drawings.

DETAILED DESCRIPTION OF THE INVENTION

This disclosure describes systems for monitoring a wine fermentation or other similar process. Many facets of wine change during the fermentation process. Parameters (e.g., pressure, temperature, density, level, turbidity, color, pH, alcohol content) may be automatically captured continuously or otherwise over time and wirelessly transferred to a database for analysis and storage. Thresholds may be set such that a winemaker can be notified when the monitored parameters are out of selected or desired range.

Figure 1:
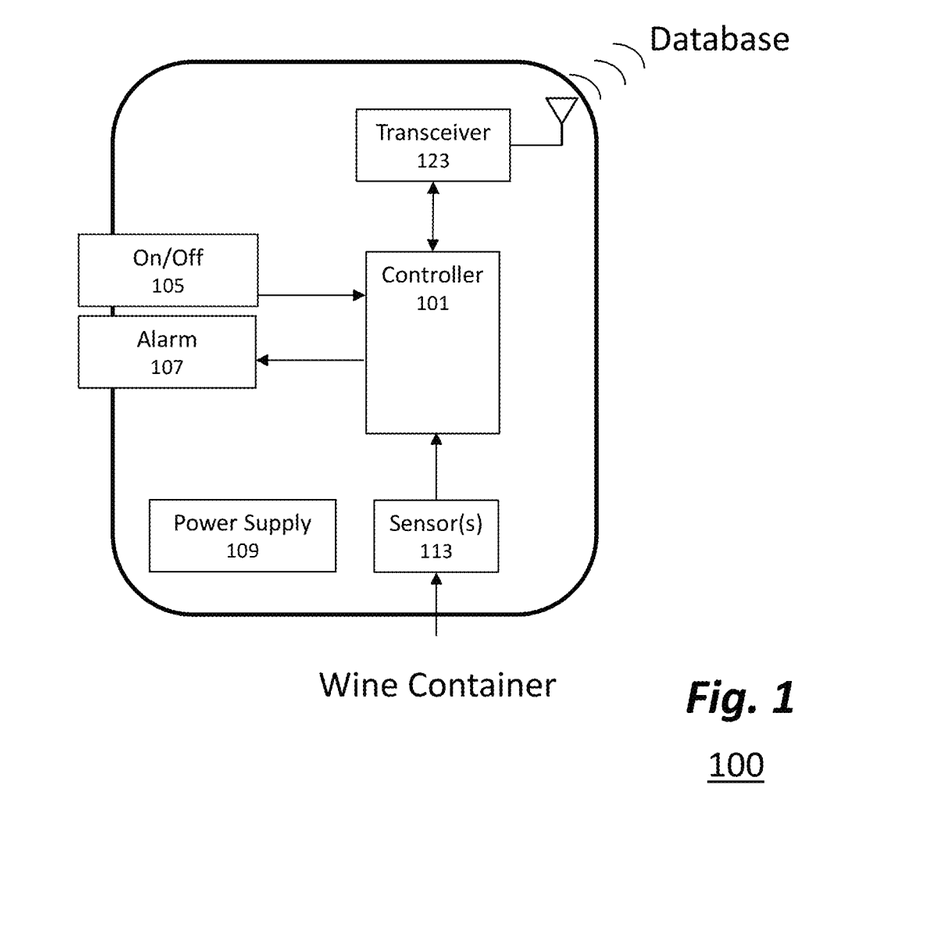
FIG. 1 illustrates components of a sensor device in accordance with an example implementation of this disclosure.

FIG. 1 illustrates components of a sensor device 100 in accordance with an example implementation of this disclosure. The depicted components of the sensor device 100 include a controller 101, an on/off switch 105, an alarm 107, a power supply 109, one or more sensor(s) 113, and a transceiver 123.

In operation, the sensor device 100 is coupled to a wine barrel or vat during a winemaking process. The temperature probe 115 measures the temperature of the wine, and the one or more sensor(s) 113 measure additional parameters (e.g., pressure, density, level, turbidity, color, pH, alcohol content) of the wine. These measurements are conveyed to the controller 101, which is operable to control a wireless transmission of the information, via transceiver 123, to a database for analysis and storage. Analysis of this information in the database may be performed by a remote device on the network. The transceiver 123 may use Bluetooth, WiFi, LoRa and/or any digital cellular standard.

The controller 101 may be operable to derive certain parameters from those supplied by the one or more sensor(s) 113. For example, a wine level may be derived according to a pressure measurement. If the power supply 109 comprises one or more batteries, for example, the microcontroller 101 may be operable to monitor and report to the database when the batteries should be replaced or recharged.

The on/off switch 105 may comprise a button. Pressing the button 105 ON can trigger the sensor device 100 to send a beacon to enable pairing with a network. Pressing button 105 OFF can trigger the sensor device 100 to store all current information in a Flash card before powering down.

The sensor device 100 may generate local alarms. The alarm 107 may convey a visual and/or an audio alarm 107. Different sounds and/or different colors may indicate various conditions. A flashing red light or a beeping may indicate a low battery. A solid yellow light may indicate a low level and a need for topping off the wine. A solid blue light may indicate that the wine below a low temperature threshold. The alarm 107 may comprise an LED. Such an LED may be incorporated into an on/off button 105. The alarm 107 may also be used to indicate the status of a pairing of the sensor device 100 to a local network.

The one or more sensor(s) 113 are operably coupled to a wine container, such as a barrel or a vat. The type of sensors used may depend of the current stage of winemaking. During fermentation, for example, multiple pressure sensors may be used to derive a change in wine density.

Figure 2:
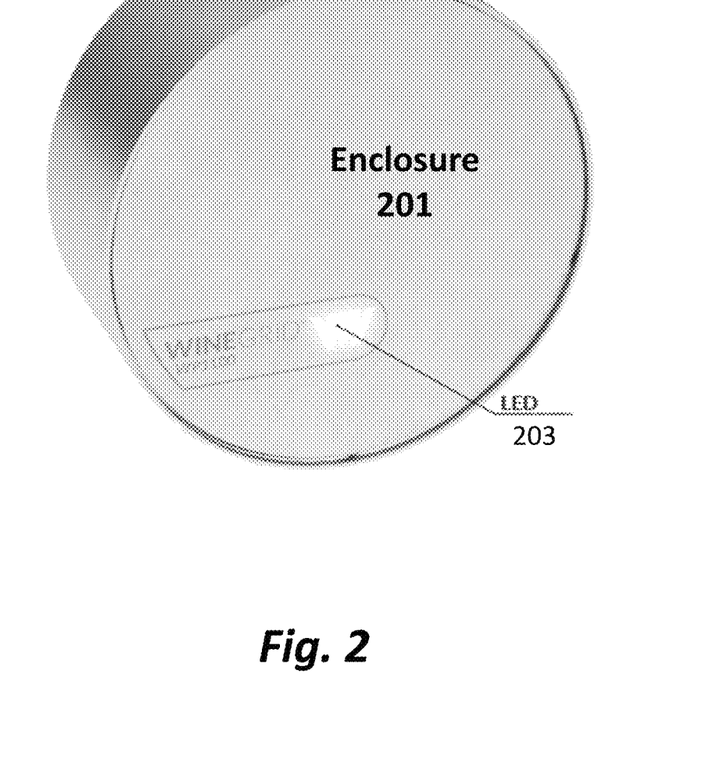
FIG. 2 illustrates a front view of a sensor device enclosure in accordance with an example implementation of this disclosure.

FIG. 2 illustrates an enclosure 201 for a sensor device 100 as described regarding FIG. 1. The enclosure comprises an LED 203 to provide an alarm. The electronic circuitry (i.e., controller 101, sensor(s) 113 and transceiver 123 as described regarding FIG. 1) may be mounted in the enclosure 201.

Figure 3:
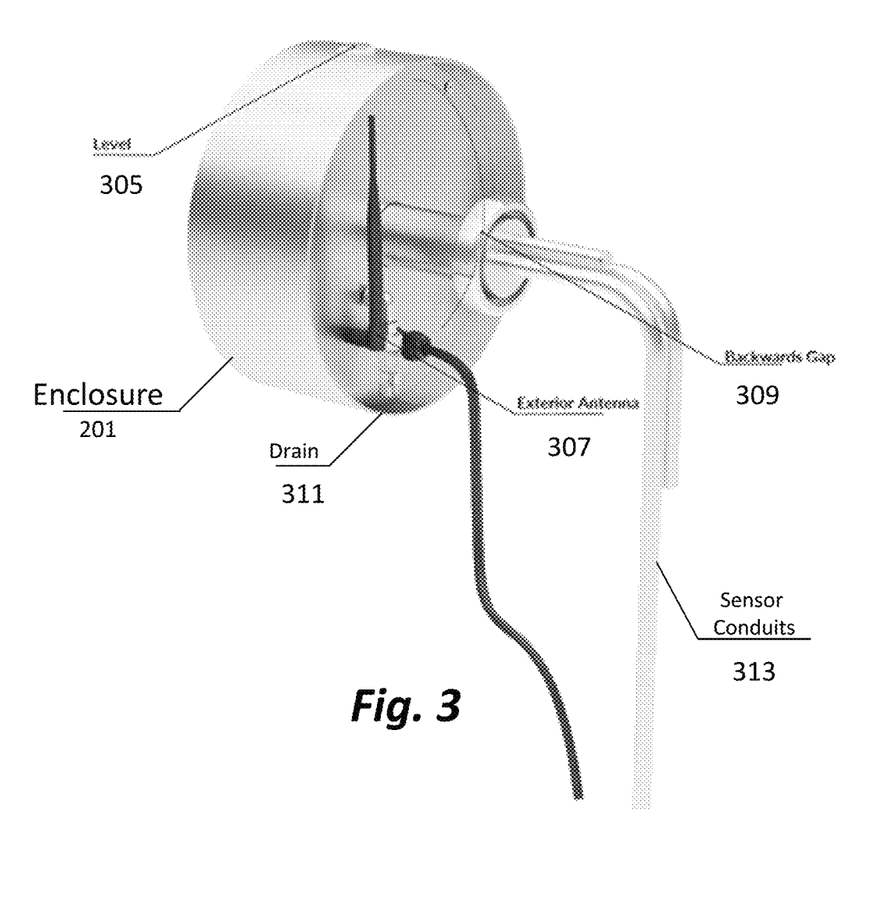
FIG. 3 illustrates a back view of a sensor device enclosure in accordance with an example implementation of this disclosure.

FIG. 3 illustrates a back view of the enclosure 201 for a sensor device 100. The depicted components coupled to the enclosure 201 include a bubble level 305, an exterior antenna 307, a backwards gap 309 with a drain hole 311, and one or more sensor(s) 313.

The backwards gap 309 provides physical space to hide and protect external hardware such as an electrical cable, a filter and the exterior antenna 307. The backwards gap 309 may comprise a pit/trench to direct water away from the enclosure 201, for example, during water jet cleaning. The drain hole 311 prevents water from gathering and entering the enclosure 201. The bubble level 305 may be used during installation to ensure vertical alignment of the sensor conduits 313.

Figure 4:
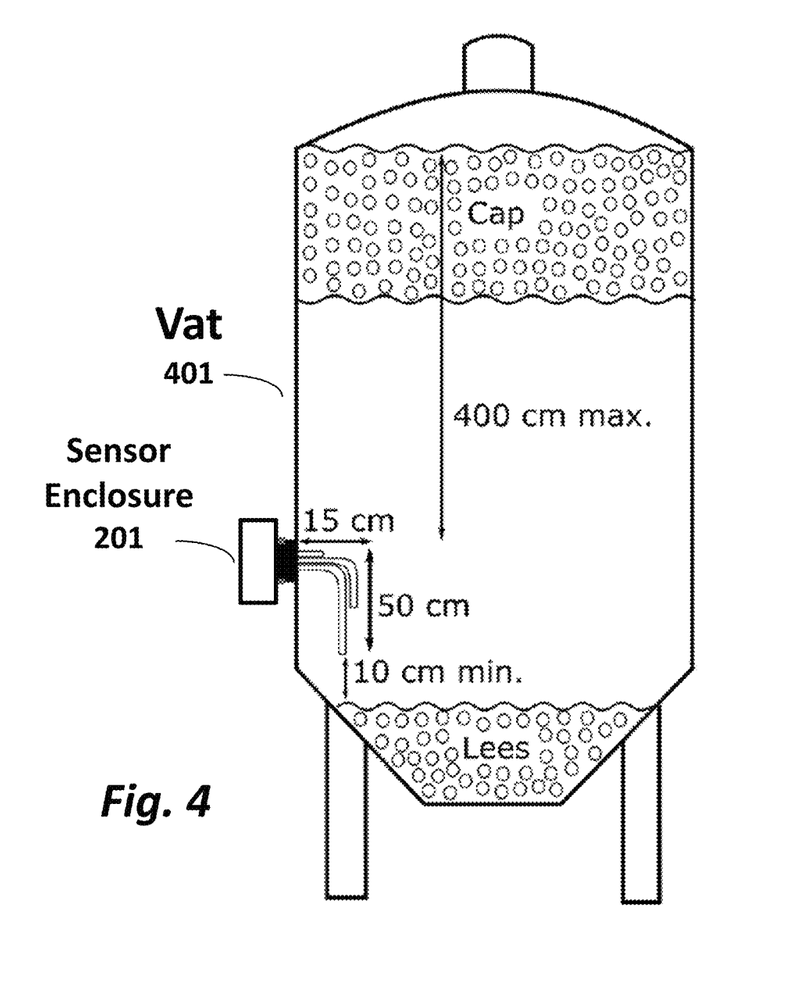
FIG. 4 illustrates a cut-away side view of a sensor system in a wine vat in accordance with an example implementation of this disclosure.

FIG. 4 illustrates a cut-away side view of a sensor system installed in a wine vat 401.

Figure 5:
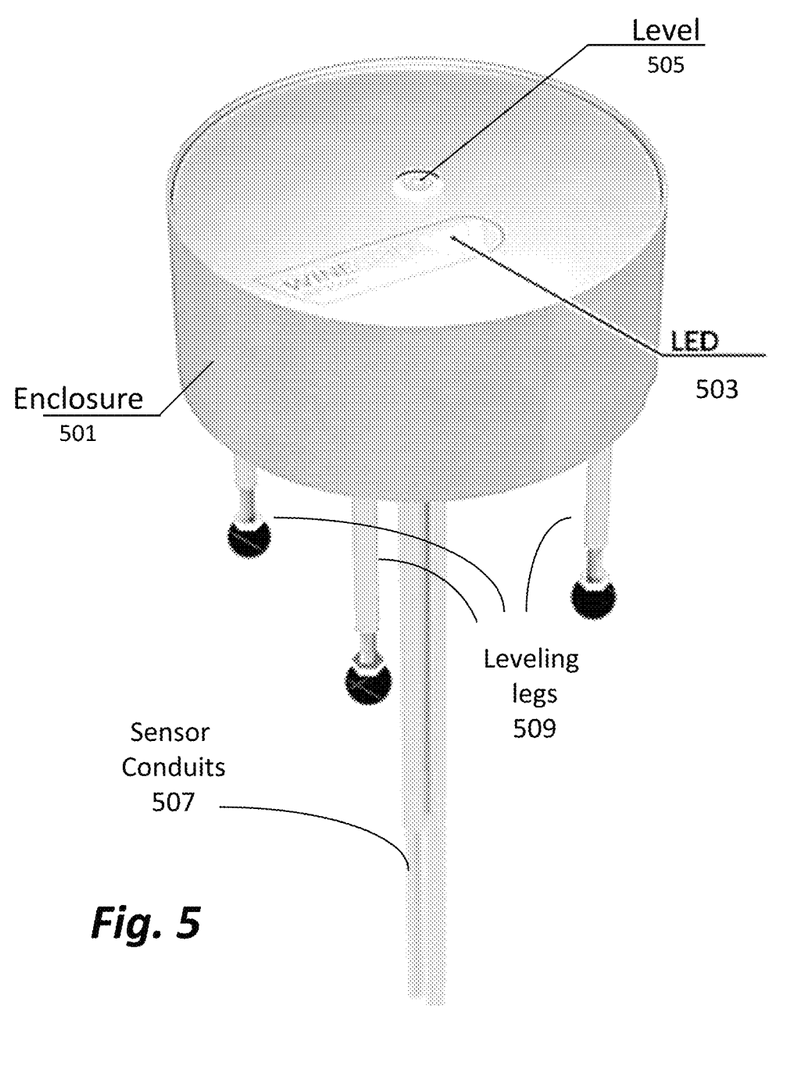
FIG. 5 illustrates a top view of a sensor device enclosure in accordance with an example implementation of this disclosure.

FIG. 5 illustrates a top view of an alternative sensor device enclosure 501. The enclosure comprises an LED 503 to provide an alarm and a bubble level 505 to ensure vertical alignment of the sensor conduits 507. The electronic circuitry (i.e., controller 101, sensor(s) 113 and transceiver 123 as described regarding FIG. 1) may be mounted in the enclosure 501. Leveling legs 509 may be adjusted to correct leveling in accordance with the bubble level 505.

Figure 6:
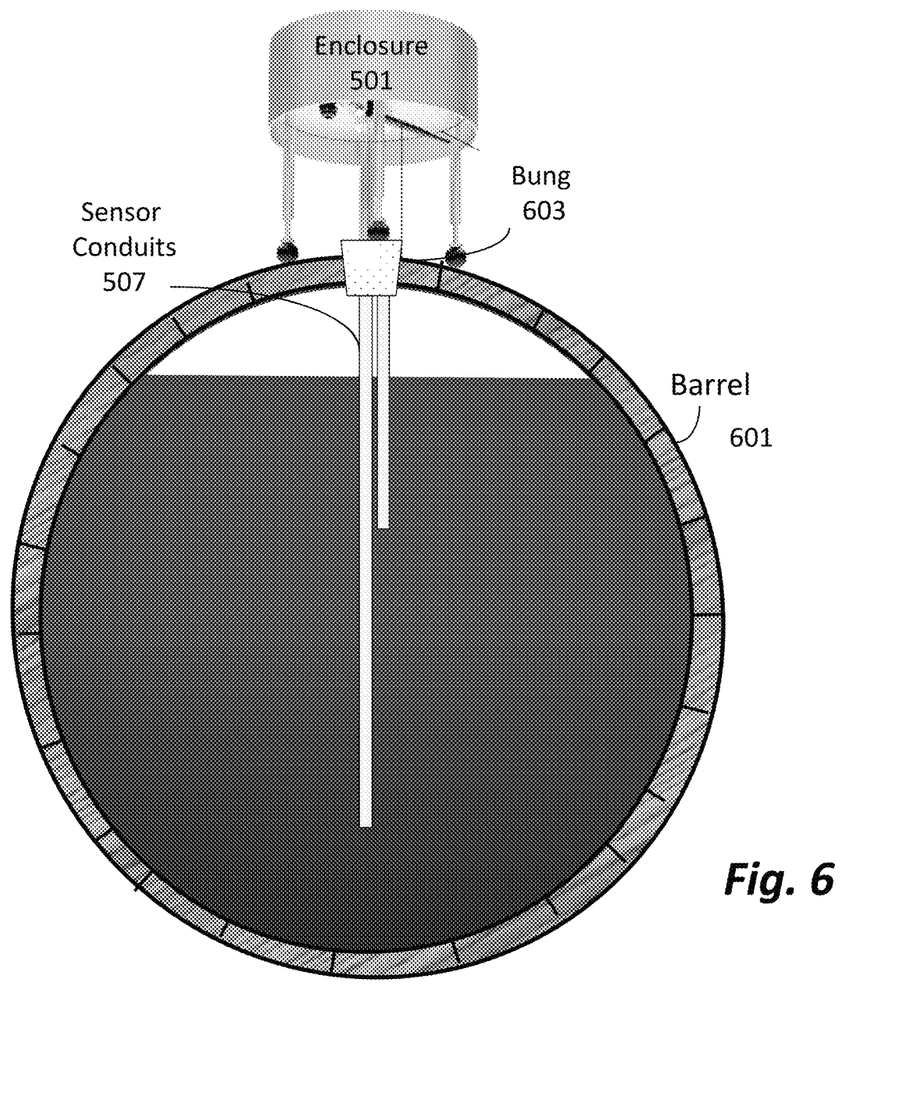
FIG. 6 illustrates a cut-away side view of a sensor system in a wine barrel in accordance with an example implementation of this disclosure.

FIG. 6 illustrates a cut-away side view of a sensor system in a wine barrel 601. The sensor system is inserted into the barrel 601 and held in place by the bung 603. One or more sensor conduits 507 are in contact with the wine. Other sensor conduits may also be in contact with the space above the wine. The sensor device enclosure 501 is visible from the outside of the wine barrel 601.

The bung 603 can be interchanged without affecting the rest of the sensor system. For example, the bung 603 and may deteriorate over time. Replacement of a silicone bung 603 is more cost effective than replacing the entire sensor system. Also, different barrels may have different sized bung holes. Replacing the silicone bung 603 allows a winemaker to use the same monitor regardless of the barrel.

Figure 7A:
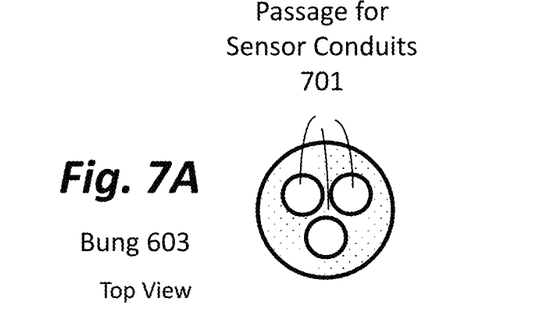
FIG. 7A illustrates a top view of a removable bung in accordance with an example implementation of this disclosure.
Figure 7B:
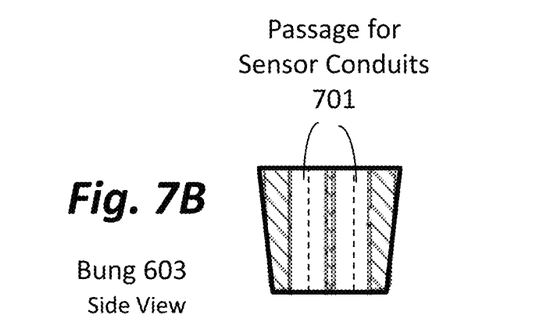
FIG. 7B illustrates a cut-away side view of a removable bung in accordance with an example implementation of this disclosure.
Figure 7C:
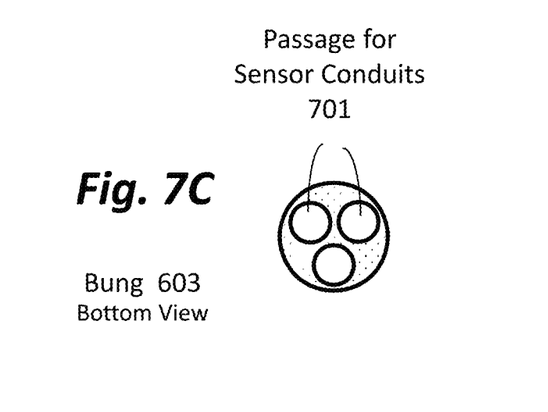
FIG. 7C illustrates a bottom view of a removable bung in accordance with an example implementation of this disclosure.

FIG. 7A illustrates a top view of the removable bung 603. FIG. 7B illustrates a cut-away side view of the removable bung 603. FIG. 7C illustrates a bottom view of the removable bung 603. A sensor system may comprise one or more sensor conduits 507. Accordingly, the bung 603 has a passage hole 701 for each sensor conduit 507. While three sensor conduits 507 are illustrated, the third passage is hidden behind the other two in FIG. 7B.

As utilized herein the terms "circuits" and "circuitry" refer to physical electronic components (i.e. hardware) and any software and/or firmware ("code") which may configure the hardware, be executed by the hardware, and or otherwise be associated with the hardware. As utilized herein, "and/or" means any one or more of the items in the list joined by "and/or". As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z". As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled or not enabled (e.g., by a user-configurable setting, factory trim, etc.).

The present invention may be realized in hardware, software, or a combination of hardware and software. The present invention may be realized in a centralized fashion in at least one computing system or in a distributed fashion where different elements are spread across several interconnected computing systems. Any kind of computing system or other apparatus adapted for carrying out the methods described herein is suited. A typical combination of hardware and software may be a general-purpose computing system with a program or other code that, when being loaded and executed, controls the computing system such that it carries out the methods described herein. Another typical implementation may comprise an application specific integrated circuit or chip.

The present invention may be realized in a non-transitory computer readable medium and/or storage medium, and/or a non-transitory machine readable medium and/or storage medium, having stored thereon, a machine code and/or a computer program having at least one code section executable by a machine and/or a computer, thereby causing the machine and/or computer to perform the processes as described herein.

While the present invention has been described with reference to certain embodiments, it will be understood by those skilled in the art that various changes may be made and equivalents may be substituted without departing from the scope of the present invention. Those skilled in the art will understand that, in addition to winemaking, the present invention may be used for making of other products (e.g., whiskey, cognac, brandy, rum, gin, vodka, tequila) without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A system for monitoring wine fermentation, wherein the system comprises:
    a sensor conduit; and
    a sensor enclosure operably coupled to the sensor conduit, wherein:
        the sensor enclosure comprises a leveling indicator operable to indicate when the sensor conduit is vertical,
        the sensor enclosure is coupled to at least three legs that enable the sensor conduit to be vertically positioned while the wine fermentation is monitored, and
        each leg is individually adjustable in height.

2. The system according to claim 1, wherein the leveling indicator comprises a bubble level.

3. The system according to claim 1, wherein the system is operable to monitor wine fermentation in a vat.

4. The system according to claim 3, wherein the sensor enclosure comprises a gap that faces the vat, and wherein the gap is operable to hide and protect external hardware coupled to the sensor enclosure.

5. The system according to claim 4, wherein the external hardware comprises one or both of a filter and an antenna.

6. The system according to claim 1, wherein the system is operable to monitor wine fermentation in a barrel.

7. The system according to claim 1, wherein the sensor conduit extends through a bung.

8. The system according to claim 7, wherein a size of the bung is selected according to a bung hole of the barrel, and wherein the bung is interchangeable with bungs of other diameters.

9. The system according to claim 7, wherein the bung is made of a material that degrades over time, and wherein a degraded bung is interchangeable with a new bung.

10. A method for monitoring wine fermentation, wherein the method comprises:
    inserting a sensor conduit into a wine container, wherein the sensor conduit is operably coupled to a sensor enclosure; and
    positioning the sensor enclosure according to a leveling indicator, wherein:
        the leveling indicator indicates when the sensor conduit is vertical,
        the sensor enclosure is coupled to a plurality of legs, and
        positioning the sensor enclosure comprises adjusting a height of at least one of the plurality of legs.

11. The method according to claim 10, wherein the leveling indicator comprises a bubble level.

12. The method according to claim 10, wherein the wine container is a vat.

13. The method according to claim 12, wherein the sensor enclosure comprises a gap that faces the vat, and wherein the gap is operable to hide and protect external hardware coupled to the sensor enclosure.

14. The method according to claim 13, wherein the external hardware comprises one or both of a filter and an antenna.

15. The method according to claim 10, wherein the wine container is a barrel.

16. The method according to claim 10, wherein the sensor conduit extends through a bung.

17. The method according to claim 16, wherein a size of the bung is selected according to a bung hole of the barrel, and wherein the method comprises:
   moving the sensor enclosure and the sensor conduit to a different barrel with a differently-sized bung hole; and
   replacing the bung with a different bung.

18. The method according to claim 16, wherein the bung is made of a material that degrades over time, and wherein the method comprises replacing a degraded bung with a new bung.

* * * * *